United States Patent
Zhu et al.

(10) Patent No.: US 6,777,413 B2
(45) Date of Patent: Aug. 17, 2004

(54) 2-[1H]-QUINOLONE AND 2-[1H]-QUINOXALONE INHIBITORS OF FACTOR XA

(75) Inventors: Bing-Yan Zhu, Belmont, CA (US); Robert M. Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 65 days.

(21) Appl. No.: 09/773,374

(22) Filed: Feb. 1, 2001

(65) Prior Publication Data

US 2002/0058657 A1 May 16, 2002

Related U.S. Application Data

(60) Provisional application No. 60/179,389, filed on Feb. 1, 2000, and provisional application No. 60/191,722, filed on Mar. 24, 2000.

(51) Int. Cl.⁷ ..................... A61K 31/495; A61K 31/47; C07D 241/36; C07D 215/16
(52) U.S. Cl. .................... 514/249; 514/228.2; 514/250; 514/259; 514/272; 514/312; 544/60; 544/284; 544/331; 544/354; 546/153
(58) Field of Search ............................. 514/228.2, 249, 514/250, 259, 272, 312; 544/60, 284, 331, 354; 546/153

(56) References Cited

U.S. PATENT DOCUMENTS 5,475,009 A * 12/1995 Chernesky et al. ......... 514/312
6,015,800 A * 1/2000 Nikam ......................... 514/85
6,410,536 B1 * 6/2002 Dudley et al. ............... 514/249

FOREIGN PATENT DOCUMENTS

| WO | WO 99/37643 | 7/1999 |
| WO | 99/50254 | 10/1999 |
| WO | WO 99/50257 | 10/1999 |
| WO | WO 01/05784 | 1/2001 |
| WO | WO 01/12600 | 2/2001 |

OTHER PUBLICATIONS

U.S. patent application Ser. No. 09/773,373, Bing–Yan Zhu et al., filed Feb. 1, 2001.

Dudley et al., "Rational Design, Synthesis, and Biological Activiety of Benzoxazinones as Novel Factor Xa Inhibitors"; *J. Med. Chem.*, vol. 43, pp. 4063–4070 (2000), Web publication date of Sep. 27, 2000.

Database WPI, Sectioni Ch. Week 199938, Derwent Publications Ltd., London, GB; AN 1999–458674, XP002168247, 1999.

* cited by examiner

*Primary Examiner*—Richard L. Raymond
*Assistant Examiner*—Tamthom N. Truong
(74) *Attorney, Agent, or Firm*—Townsend and Townsend and Crew LLP

(57) ABSTRACT

Novel compounds of general formula I:

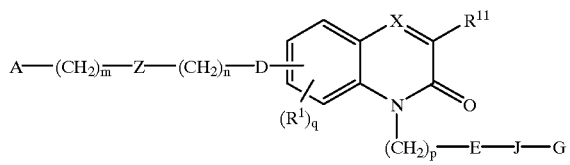

including their pharmaceutically acceptable isomers, salts, hydrates, solvates and prodrug derivative having activity against mammalian factor Xa is described. Compositions containing such compounds are also described. The compounds and compositions are useful in vitro or in vivo for preventing or treating conditions in mammals characterized by undesired thrombosis.

12 Claims, No Drawings

2-[1H]-QUINOLONE AND 2-[1H]-QUINOXALONE INHIBITORS OF FACTOR XA

RELATED APPLICATIONS

This application claims benefit of priority under 35 U.S.C. §119(e) of U.S. Provisional Application No. 60/179,389 filed on Feb. 1, 2000 and U.S. Provisional Application No. 60/191,722 filed on Mar. 24, 2000, each of which is incorporated in its entirety by reference.

FIELD OF THE INVENTION

The invention relates to novel bicyclic lactam ring system containing compounds including their pharmaceutically acceptable isomers, salts, hydrates, solvates and prodrug derivatives, and pharmaceutically acceptable compositions thereof which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel bicyclic lactam ring system containing compounds including their pharmaceutically acceptable isomers, salts, hydrates, solvates and prodrug derivatives, and pharmaceutically acceptable compositions thereof which are useful as potent and specific inhibitors of blood coagulation in mammals. In yet another aspect, the invention relates to methods for using these inhibitors as diagnostic or therapeutic agents for disease states in mammals characterized by undesired thrombosis or coagulation disorders.

BACKGROUND OF THE INVENTION

Hemostasis, the control of bleeding, occurs by surgical means, or by the physiological properties of vasoconstriction and coagulation. The invention is particularly concerned with blood coagulation and ways in which it assists in maintaining the integrity of mammalian circulation after injury, inflammation, disease, congenital defect, dysfunction or other disruption. Under normal hemostatic circumstances, the body maintains an acute balance of clot formation and clot removal (fibrinolysis). The blood coagulation cascade involves the conversion of a variety of inactive enzymes (zymogens) into active enzymes which ultimately convert the soluble plasma protein fibrinogen into an insoluble matrix of highly cross-linked fibrin. Davie, E. J. et al., "The Coagulation Cascade: Initiation, Maintenance and Regulation", Biochemistry, 30, 10363–10370 (1991). These plasma glycoprotein zymogens include Factor XII, Factor XI, Factor IX, Factor X, Factor VII, and prothrombin. Blood coagulation follows either the intrinsic pathway, where all of the protein components are present in blood, or the extrinsic pathway, where the cell membrane protein tissue factor plays a critical role. Clot formation occurs when fibrinogen is cleaved by thrombin to form fibrin. Blood clots are composed of activated platelets and fibrin.

Blood platelets which adhere to damaged blood vessels are activated and incorporated into the clot and thus play a major role in the initial formation and stabilization of hemostatic "plugs". In certain diseases of the cardiovascular system, deviations from normal hemostasis push the balance of clot formation and clot dissolution towards life-threatening thrombus formation when thrombi occlude blood flow in coronary vessels (myocardial infarctions) or limb and pulmonary veins (venous thrombosis). Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Under normal circumstances, thrombin can also play an anticoagulant role in hemostasis through its ability to convert protein C into activated protein C (aPC) in a thrombomodulin-dependent manner. However, in atherosclerotic arteries these thrombin activities can initiate the formation of a thrombus, which is a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth muscle cell proliferation and may therefore be involved in a variety of proliferative responses such as restenosis after angioplasty and graft induced atherosclerosis. In addition, thrombin is chemotactic for leukocytes and may therefore play a role in inflammation. (Hoover, R. J., et al. Cell, 14, 423 (1978); Etingin, O. R., et al., Cell, 61 657 (1990). These observations indicate that inhibition of thrombin formation or inhibition of thrombin itself may be effective in preventing or treating thrombosis, limiting restenosis and controlling inflammation.

Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kd precursor and is converted to the active form, Factor Xa, in both the extrinsic and intrinsic blood coagulation pathways. Factor X is a member of the calcium ion binding, gamma carboxyglutamyl (Gla)-containing, vitamin K dependent, blood coagulation glycoprotein family, which also includes Factors VII and IX, prothrombin, protein C and protein S (Furie, B., et al., Cell, 53, 505 (1988)). The activity of Factor Xa in effecting the conversion of prothrombin to thrombin is dependent on its inclusion in the prothrombinase complex.

The prothrombinase complex converts the zymogen prothromnbin into the active procoagulant thrombin. It is therefore understood that Factor Xa catalyzes the next-to-last step in the blood coagulation cascade, namely the formation of the serine protease thrombin. In turn, thrombin then acts to cleave soluble fibrinogen in the plasma to form insoluble fibrin.

The location of the prothrombinase complex at the convergence of the intrinsic and extrinsic coagulation pathways, and the resulting significant amplification of thrombin generation (several hundred-thousand fold faster in effecting the conversion of prothrombin to thrombin than Factor Xa in soluble form) mediated by the complex at a limited number of targeted catalytic units present at vascular lesion sites, suggests that inhibition of thrombin generation is a desirable method to block uncontrolled procoagulant activity. It has been suggested that compounds which selectively inhibit factor Xa may be useful as in vitro diagnostic agents, or for therapeutic, administration in certain thrombotic disorders, see e.g., WO 94/13693. Unlike thrombin, which acts on a variety of protein substrates as well as at a specific receptor, factor Xa appears to have a single physiologic substrate, namely prothrombin.

Plasma contains an endogenous inhibitor of both the factor VIIa-tissue factor (TF) complex and factor Xa called tissue factor pathway inhibitor (TFPI). TFPI is a Kunitz-type protease inhibitor with three tandem Kunitz domains. TFPI inhibits the TF/fVIIa complex in a two-step mechanism which includes the initial interaction of the second Kunitz domain of TFPI with the active site of factor Xa, thereby inhibiting the proteolytic activity of factor Xa. The second step involves the inhibition of the TF/fVIIa complex by formation of a quaternary complex TF/fVIIa/TFPI/fXa as described by Girard, T. J. et al., "Functional Significance of the Kunitz-type Inhibitory Domains of Lipoprotein-associated Coagulation Inhibitor", Nature, 338, 518–520 (1989).

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988).

Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593–596 (1990).

Other polypeptide type inhibitors of factor Xa have been reported including the following: Condra, C. et al., "Isolation and Structural Characterization of a Potent Inhibitor of Coagulation Factor Xa from the Leech *Haementeria ghilianii*", Thromb. Haemost., 61, 437–441 (1989); Blankenship, D. T. et al., "Amino Acid Sequence of Ghilanten: Anti-coagulant-antimetastatic Principle of the South American Leech, *Haementeria ghilianii*", Biochem. Biophys. Res. Commun. 166, 1384–1389 (1990); Brankamp, R. G. et al., "Ghilantens: Anticoagulants, Anti-metastatic Proteins from the South American Leech *Haementeria ghilianii*", J. Lab. Clin. Med., 115, 89–97 (1990); Jacobs, J. W. et al., "Isolation and Characterization of a Coagulation Factor Xa Inhibitor from Black Fly Salivary Glands", Thromb. Haemost., 64, 235–238 (1990); Rigbi, M. et al., "Bovine Factor Xa Inhibiting Factor and Pharmaceutical Compositions Containing the Same", European Patent Application, 352,903; Cox, A. C., "Coagulation Factor X Inhibitor From the Hundred-pace Snake *Deinagkistrodon acutus*, venom", Toxicon, 31, 1445–1457 (1993); Cappello, M. et al., "Ancylostoma Factor Xa Inhibitor: Partial Purification and its Identification as a Major Hookworm-derived Anticoagulant In Vitro", J. Infect. Dis., 167, 1474–1477 (1993); Seymour, J. L. et. al., "Ecotin is a Potent Antico-agulant and Reversible Tight-binding Inhibitor of Factor Xa", Biochemistry 33, 3949–3958 (1994).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); Miyadera, A. et al., Japanese Patent Application JP 6327488; Nagahara, T. et al., "Dibasic (Amidinoaryl) propanoic Acid Derivatives as Novel Blood Coagulation Factor Xa Inhibitors", J. Med. Chem., 37, 1200–1207 (1994); Vlasuk, G. P. et al., "Inhibitors of Thrombosis", WO 93/15756; and Brunck, T. K. et al., "Novel Inhibitors of Factor Xa", WO 94/13693.

A number of inhibitors of trypsin-like enzymes (such as trypsin, enterokinase, thrombin, kallikrein, plasmin, urokinase, plasminogen activators and the like) have been the subject of disclosures. For example, Austen et al., U.S. Pat. No. 4,593,018 describes oligopeptide aldehydes which are specific inhibitors of enterokinase; Abe et al., U.S. Pat. No. 5,153,176 describes tripeptide aldehydes which have inhibitory activity against multiple serine proteases such as plasmin, thrombin, trypsin, kallikrein, factor Xa, urokinase, etc.; Brunck et al., European Publication WO 93/14779 describes substituted tripeptide aldehydes that are specific inhibitors of trypsin; U.S. Pat. Nos. 4,316,889, 4,399,065, 4,478,745 all disclose arginine aldehyde inhibitors of thrombin; Balasubramanian et al., U.S. Pat. No. 5,380,713 describes di- and tripeptide aldehydes which are useful for anti-trypsin and anti-thrombin activity; Webb et al., U.S. Pat. No. 5,371,072 describes tripeptide alpha-keto-amide derivatives as inhibitors of thrombosis and thrombin; Gesellchen et al., European Patent Publications 0479489 A2 and 0643073 A, describe tripeptide thrombin inhibitors; Veber et al., European Publication WO 94/25051 describes 4-cyclohexylamine derivatives which selectively inhibit thrombin over other trypsin-like enzymes; Tapparelli et al., J. Biol. Chem. 268, 4734–4741 (1993) describe selective peptide boronic acid derivatives as inhibitors of thrombin.

Alternatively, agents which inhibit the vitamin K-dependent carboxylase enzyme, such as coumarin, have been used to treat coagulation disorders.

There exists a need for effective therapeutic agents for the regulation of hemostasis, and for the prevention and treatment of thrombus formation and other pathological processes in the vasculature induced by thrombin such as restenosis and inflammation.

SUMMARY OF THE INVENTION

The present invention provides novel bicyclic lactam ring system containing compounds including their pharmaceutically acceptable isomers, salts, hydrates, solvates and prodrug derivatives, which have particular biological properties and are useful as potent and specific inhibitors of blood coagulation in mammals. The invention also provides compositions containing such compounds. The compounds of the invention may be used as diagnostic reagents or as therapeutic agents for disease states in mammals which have coagulation disorders. Thus, the invention further provides methods for preventing or treating a condition in a mammal characterized by undesired thrombosis by administration of a therapeutically effective amount of a compound of the invention and a pharmaceutically acceptable carrier. Optionally, the methods of the invention comprise administering a pharmaceutical composition of the invention in combination with an additional therapeutic agent such as an antithrombotic and/or a thrombolytic agent and/or an anticoagulant. According to the invention, such conditions include, for example, any thrombotically mediated acute coronary or cerebrovascular syndrome, any thrombotic syndrome occurring in the venous system, any coagulopathy, and any thrombotic complications associated with extracorporeal circulation or instrumentation. The invention still further provides a method for inhibiting the coagulation of biological samples (e.g. stored blood products and samples).

The invention provides a compound of general formula I:

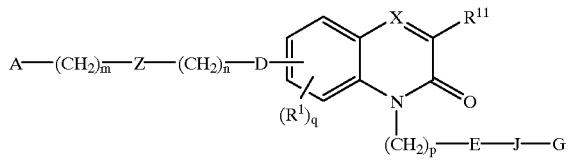

wherein:

A is a member selected from the group consisting of: $R^2$, —$NR^3R^4$, —$C(=O)NR^3R^4$,

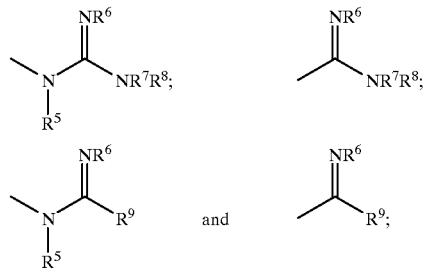

where $R^2$, $R^3$, $R^4$, $R^5$, $R^6$, $R^7$, $R^8$, and $R^9$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $R^6$ taken with either of $R^7$ and $R^8$, and/or $R^7$ taken with $R^8$, can each form a 5 to 6 membered heterocyclic ring containing from 1 to 4 atoms selected from the group consisting of N, O and S;

m is an integer from 0–3, preferably 0–2;

Z is a member selected from the group consisting of a direct link, $C_{1-8}$alkyl, $C_{3-8}$cycloalkyl, $C_{2-8}$alkenyl, $C_{2-8}$alkynyl, $C_{1-8}$carbocyclic aryl, or a five to ten membered heterocyclic ring system containing 1–4 heteroatoms selected from the group consisting of N, O and S;

n is an integer from 0–3, preferably 0–2;

D is a member selected from the group consisting of a direct link, —$CH_2$—, —O—, —$N(R^2)$—, —$C(=O)$—, —S—, —$SO_2$—, —$SO_2$—$N(R^2)$—, —$N(R^2)$—$SO_2$—, —$OC(=O)$—, —$C(=O)O$—, —$C(=O)$—$N(R^2)$— and —$N(R^2)$—$C(=O)$—, where $R^2$ is as described above;

$R^1$ is a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-$C(=O)OH$, $C_{0-8}$alkyl-$C(=O)O$—$C_{1-8}$alkyl, —CN, —$NO_2$, $C_{0-8}$alkyl-OH, $C_{0-8}$alkyl-SH, —$C(=O)NR^2R^3$, —O—$R^2$ and —O—$C(=O)R^2$, an unsubstituted amino group, a mono or disubstituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, —$SO_2R^2$, $C_{0-8}$alkyl-$C(=O)OH$ and $C_{0-8}$alkyl-$C(=O)O$—$C_{1-8}$alkyl, where $R^2$ and $R^3$ is as described above;

q is an integer from 0–3, preferably 0–2;

X is N or —$CR^{12}$;

$R^{11}$ and $R^{12}$ are independently a member selected from the group consisting of H, $C_{1-8}$alkyl, $C_{2-8}$alkenyl, $C_{2-8}$alkynyl, $C_{3-8}$cycloalkyl, $C_{6-12}$carbocyclic aryl, $C_{1-6}$alkylaryl, $C_{1-6}$alkyl-$C_{3-8}$cycloalkyl, —O—$R^2$, —O—$C(=O)R^2$, —$C_{1-8}$alkyl-O—$R^{10}$, —$C_{1-8}$alkyl-O—$C(=O)R^{10}$, —$C_{1-8}$alkyl-$C(=O)OR^{10}$, —$C_{1-8}$alkyl-O—$C(=O)OR^{10}$, —$C_{1-8}$alkyl-$C(=O)NR^{10}R^{10}$, —$C_{1-8}$alkyl-$NR^{10}R^{10}$, —$C_{1-8}$alkyl-$NR^{10}C(=O)R^{10}$, —$SR^{10}$, where $R^2$ is as described above and $R^{10}$ is a member selected from the group consisting of H, $C_{1-8}$alkyl, $C_{2-8}$alkenyl, $C_{2-8}$alkynyl, and wherein when two $R^{10}$ groups are present they may be taken together to form a saturated or unsaturated ring with the atom to which they are both attached, preferably a partially or fully saturated ring;

p is an integer from 0–3, preferably 0–2;

E is a member selected from the group consisting of a direct link, —O—, —$N(—R^{11})$—, where $R^{11}$ is as set forth above, phenylene, a bivalent 5 to 12 member heteroaryl group containing 1 to 4 heteroatoms selected from the group consisting of N, O and S, and a five to ten membered nonaromatic bivalent heterocyclic ring system containing 1–4 heteroatoms selected from the group consisting of N, O and S, wherein said heteroaryl and said nonaromatic heterocyclic ring structure may be independently substituted by from 0 to 5 $R^{14}$ groups and each $R^{14}$ group is independently defined the same as the substituents set forth above for the $R^1$ group;

J is a member selected from the group consisting of a direct link, a bivalent $C_{3-8}$cycloalkyl group, phenylene, a 5 to 12 member bivalent heteroaryl group containing 1 to 4 heteroatoms selected from the group consisting of N, O and S, and a five to ten membered nonaromatic bivalent heterocyclic ring system containing 1–4 heteroatoms selected from the group consisting of N, O and S wherein said heteroaryl and said nonaromatic heterocyclic ring structure may be independently substituted by from 0 to 5 $R^{14}$ groups and each $R^{14}$ group is independently defined the same as the substituents set forth above for the $R^1$ group;

G is a member selected from the group consisting of: H; —CN; —$OR^{17}$;

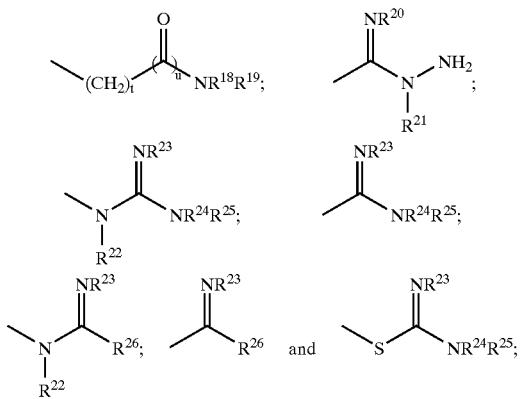

wherein t is an integer from 0 to 6, u is the integer 0 or 1, and $R^{17}$, $R^{18}$, $R^{19}$, $R^{20}$, $R^{21}$, $R^{22}$, $R^{23}$, $R^{24}$, $R^{25}$ and $R^{26}$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $r^{18}$ taken with $R^{19}$, $R^{22}$ taken with either of $R^{24}$ and $R^{25}$, and $R^{24}$ taken with $R^{25}$, can each independently form a 5 to 6 membered heterocyclic ring containing from 1 to 4 atoms selected from the group consisting of N, O and S;

with the proviso that when G is H, —CN, —$OR^{17}$, either E or J must contain at least one N atom;

and all pharmaceutically acceptable isomers, salts, hydrates, solvates and prodrug derivatives thereof.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "lower alkyl" refers to a $C_1$–$C_8$ unsubstituted alkyl group unless a substituent(s) is specified. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic nonaromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are nonaromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, naphthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as nonaromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benzitriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolaminie, trimethamine, dicyclohexylamine, choline, and caffeine.

"Biological property" for the purposes herein means an in vivo effector or antigenic function or activity that is directly or indirectly performed by a compound of the invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of the invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of the invention, may be in one of two configurations (R or S) and both are within the scope of the present invention.

Compounds

The invention provides a compound of general formula I:

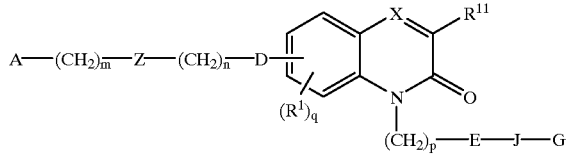

wherein:

A is a member selected from the group consisting of: $R^2$, $-NR^3R^4$, $-C(=O)NR^3R^4$,

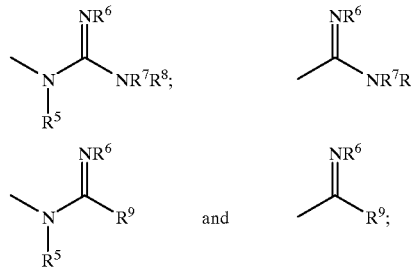

where $R^2$, $R^3$, $R^4$, $R^5$, $R^6$, $R^7$, $R^8$, and $R^9$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $r^6$ taken with either of $R^7$ and $R^8$, and/or $R^7$ taken with $R^8$, can each form a 5 to 6 membered heterocyclic ring containing from 1 to 4 atoms selected from the group consisting of N, O and S; preferably, $R^2$, $R^3$, $R^4$, $R^5$, $R^6$, $R^7$, $R^8$, and $R^9$ are independently selected from the group consisting of H, —OH, $C_{1-6}$alkyl, $C_{3-8}$cycloalkyl, $C_{6\ 10}$aryl, a five to ten membered heterocyclic ring system containing 1–4 heteroatoms selected from the group consisting of N, O and S; and $C_{1-4}$alkylheterocyclic ring system having in the ring system 5 to 10 atoms with 1 to 4 of such atoms being selected from the group consisting of N, O and S; where $R^6$ taken with either of $R^7$ and $R^8$, and/or $R^7$ taken with $R^8$, can each form a 5 to 6 membered heterocyclic ring containing from 1 to 4 atoms selected from the group consisting of N, O and S;

m is an integer from 0–3, preferably 0–2;

Z is a member selected from the group consisting of a direct link, $C_{1-8}$alkyl, $C_{3-8}$cycloalkyl, $C_{2-8}$alkenyl, $C_{2-8}$alkynyl, $C_{1-8}$carbocyclic aryl, or a five to ten membered heterocyclic ring system containing 1–4 heteroatoms selected from the group consisting of N, O and S; preferably, Z is a member selected from the group consisting of a direct link, $C_{1-6}$alkyl, $C_{3-8}$cycloalkyl, $C_{1-6}$alkenyl, $C_{6-10}$aryl, or a five to ten membered heterocyclic ring system containing 1–4 heteroatoms selected from the group consisting of N, O and S;

n is an integer from 0–3, preferably 0–2;

D is a member selected from the group consisting of a direct link, $-CH_2-$, $-O-$, $-N(R^2)-$, $-C(=O)-$, $-S-$, $-SO_2-$, $-SO_2-N(R^2)-$, $-N(R^2)-SO_2-$, $-OC(=O)-$, $-C(=O)O-$, $-C(=O)-N(R^2)-$ and $-N(R^2)-C(=O)-$, where $R^2$ is as described above; preferably, D is a member selected from the group consisting of a direct link, $-CH_2-$, $-O-$, $-NR^2$, $-C(=O)-$, $-S-$, $-SO_2-$, $-SO_2N^2-NR^2-SO_2$, $-OC(=O)-$, $-C(=O)NR^2$, and $-NR^2-C(=O)-$, where $R^2$ is as described above;

$R^1$ is a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-$C(=O)OH$, $C_{0-8}$alkyl-$C(=O)O-C_{1-8}$alkyl, $-CN$, $-NO_2$, $C_{0-8}$alkyl-OH, $C_{0-8}$alkyl-SH, $-C(=O)NR^2R^3$, $-O-R^2$ and $-O-C(=O)R^2$, an unsubstituted amino group, a mono- or di-substituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, $-SO_2R^2$, $C_{0-8}$alkyl-$C(=O)OH$ and $C_{0-8}$alkyl-$C(=O)O-C_{1-8}$alkyl; preferably, $R^1$ is H, $C_{1-6}$alkyl, halogen, $-C(=O)OH$, an unsubstituted amino group, a mono or disubstituted amino group, $-CN$, $-NO_2$, $-OH$, $-C(=O)NR^2R^3$, $-O-R^2$ and $-O-C(=O)R^2$, where $R^2$ and $R^3$ is as described above;

q is an integer from 0–3, preferably 0–2;

X is N or $-CR^{12}$;

$R^{11}$ and $R^{12}$ are independently a member selected from the group consisting of H, $C_{1-8}$alkyl, $C_{2-8}$alkenyl, $C_{2-8}$alkynyl, $C_{3-8}$cycloalkyl, $C_{6-12}$carbocyclic aryl, $C_{1-6}$alkylaryl, $C_{1-6}$alkyl-$C_{3-8}$cycloalkyl, $-O-R^2$, $-O-C(=O)R^2$, $-C_{1-8}$alkyl-$O-R^{10}$, $-C_{1-8}$alkyl-$O-C(=O)R^{10}$, $-C_{1-8}$alkyl-$C(=O)OR^{10}$, $-C_{1-8}$alkyl-$O-C(=O)OR^{10}$, $-C_{1-8}$alkyl-$C(=O)NR^{10}R^{10}$, $-C_{1-8}$alkyl-$NR^{10}R^{10}$, $-C_{1-8}$alkyl-$NR^{10}C(=O)R^{10}$, $-SR^{10}$, where $R^2$ is as described above and $R^{10}$ is a member selected from the group consisting of H, $C_{1-8}$alkyl, $C_{2-8}$alkenyl, $C_{2-8}$alkynyl, and wherein when two $R^{10}$ groups are present they may be taken together to form a saturated or unsaturated ring with the atom to which they are both attached, preferably a partially or fully saturated ring; preferably, $R^{11}$ and $R^{12}$ are independently a member selected from the group consisting of H, $C_{1-6}$alkyl, $C_{3-8}$cycloalkyl, $C_{6-10}$aryl, $C_{1-4}$alkylaryl, $C_{1-4}$alkyl-$C_{3-8}$cycloalkyl, $-O-R^2$, $-O-C(=O)R^2$, $-C_{1-6}$alkyl-$O-R^{10}$, $-C_{1-6}$alkyl-$O-C(=O)R^{10}$, $-C_{1-8}$alkyl-$C(=O)$ $OR^{10}$, $-C_{1-6}$alkyl-$O-C(=O)OR^{10}$, $-C_{1-6}$alkyl-$C(=O)NR^{10}R^{10}$, $-C_{1-6}$alkyl-$NR^{10}R^{10}$, $-C_{1-6}$alkyl-$NR^{10}C(=O)R^{10}$, $-SR^{10}$, where $R^2$ is as described above and $R^{10}$ is a member selected from the group consisting of H, $C_{1-6}$alkyl, and wherein when two $R^{10}$ groups are present they may be taken together to form a saturated or unsaturated ring with the atom to which they are both attached;

p is an integer from 0–3, preferably 0–2;

E is a member selected from the group consisting of a direct link, $-O-$, $-N(-R^{11})-$, where $R^{11}$ is as set forth above, phenylene, a bivalent 5 to 12 member heteroaryl group containing 1 to 4 heteroatoms selected from the group consisting of N, O and S, and a five to ten membered nonaromatic bivalent heterocyclic ring system containing 1–4 heteroatoms selected from the group consisting of N, O and S, wherein said heteroaryl and said nonaromatic heterocyclic ring structure may be independently substituted by from 0 to 5 $R^{14}$ groups and each $R^{14}$ group is independently defined the same as the substituents set forth above for the $R^1$ group;

J is a member selected from the group consisting of a direct link, a bivalent $C_{3-8}$cycloalkyl group, phenylene, a 5 to 12 member bivalent heteroaryl group containing 1 to 4 heteroatoms selected from the group consisting of N, O and S, and a five to ten membered nonaromatic bivalent heterocyclic ring system containing 1–4 heteroatoms selected from the group consisting of N, O and S wherein said heteroaryl and said nonaromatic heterocyclic ring structure may be independently substituted by from 0 to 5 $R^{14}$ groups and each $R^{14}$ group is independently defined the same as the substituents set forth above for the $R^1$ group;

G is a member selected from the group consisting of: H; —CN; —$OR^{17}$;

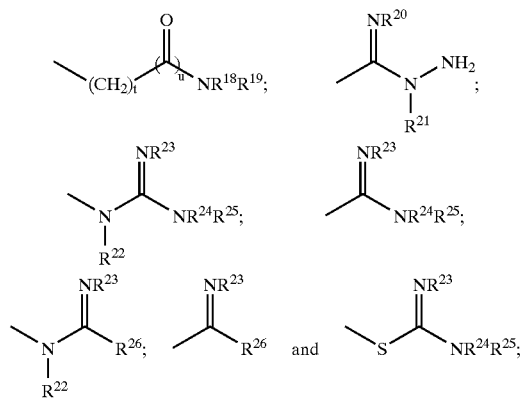

wherein t is an integer from 0 to 6, u is the integer 0 or 1, and $R^{17}$, $R^{18}$, $R^{19}$, $R^{20}$, $R^{21}$, $R^{22}$, $R^{23}$, $R^{24}$, $R^{25}$ and $R^{26}$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $r^{18}$ taken with $R^{19}$, $R^{22}$ taken with either of $R^{24}$ and $R^{25}$, and $R^{24}$ taken with $R^{25}$, can each independently form a 5 to 6 membered heterocyclic ring containing from 1 to 4 atoms selected from the group consisting of N, O and S;

with the proviso that when G is H, —CN, —$OR^{17}$, either E or J must contain at least one N atom;

and all pharmaceutically acceptable isomers, salts, hydrates, solvates and prodrug derivatives thereof.

In a preferred embodiment, the present invention provides a compound of formula II:

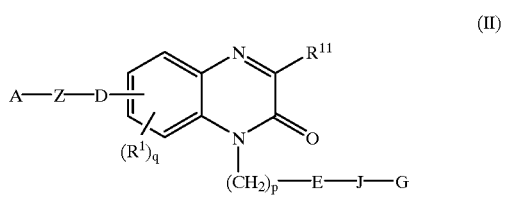

wherein A, Z, D, $R^1$, q, $R^{11}$, E, J, and G are each as set forth above and p is an integer from 0 to 2, and all pharmaceutically acceptable isomers, salts, hydrates, solvates and prodrug derivatives thereof.

In another preferred embodiment, the invention provides a compound of formula IIa:

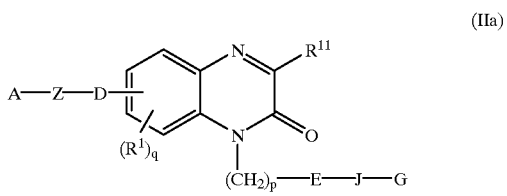

wherein:

q is an integer from 0–3, preferably, 0;

p is an integer from 0–3, preferably, 0–2;

D is a member selected from the group consisting of: —$CH_2$—, —O—, —N $R^2$, —C(=O)—, —S—, —$SO_2$—, —$SO_2$—$NR^2$, —$NR^2$—$SO_2$, —OC(=O)—, —C(=O)$NR^2$, and —$NR^2$—C(=O)—; preferably a member selected from the group consisting of: —$CH_2$—, —O—, —$NR^2$, —C(=O)—, —S—, —$SO_2$—; and A, Z, $R^2$, $R^1$, $R^{11}$, E, J and G are each as defined in formula I as set forth above.

Further preferred are compounds of formula III:

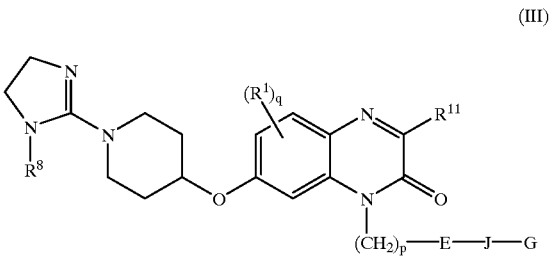

In formula III, q is an integer from 1–3 and $R^8$, $R^1$, $R^{11}$, p, E, J and G are each as defined in formula II as set forth above.

Particularly preferred compounds of formula III are compounds wherein $R^1$ and $R^8$ are each independently lower alkyl and $R^{11}$ is hydrogen or is a $C_1$ to $C_8$ alkyl group, particularly preferred cycloalkyl groups are members selected from the group consisting of cyclopropyl, cyclobutyl, cyclopentyl, cyclohexyl. Further preferred are compounds of formula III wherein one or more of E and J is independently a phenylene, heteroaryl or a heterocyclic group as defined above with respect to formula II, especially a phenylene, heteroaryl or heterocyclic member selected from the group consisting of phenyl, thiophene, furan, benzofuran, benzothiophene, pyridine, other heterocyclic bicyclic rings as defined above for formula II, and the like. When only one of E or J is a phenylene, heteroaryl or heterocyclic member, the other is preferably a direct link. More preferred compounds are compounds of formula III wherein q is zero and $R^8$ is lower alkyl group.

Even more preferred compounds of formula III are such compounds according to formula IIIa wherein $R^1$ and $R^{11}$ are each independently hydrogen or $C_1$ to $C_6$ alkyl as set forth in Table 1, below.

TABLE 1

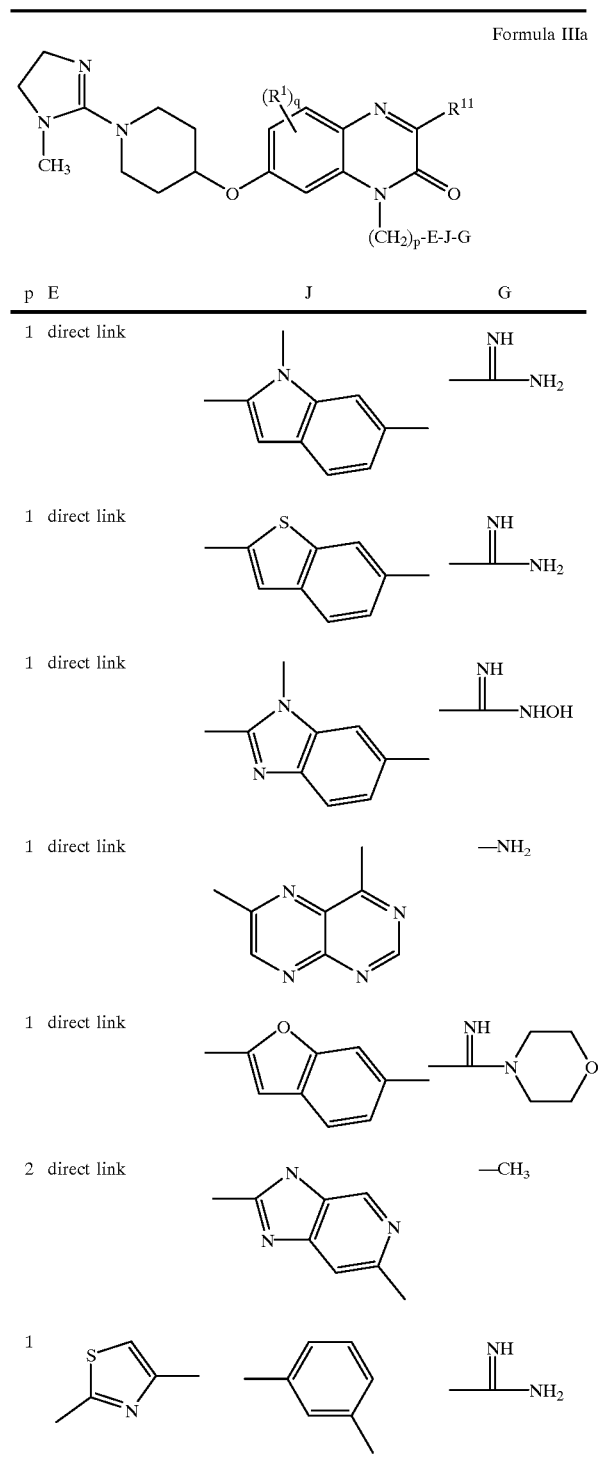

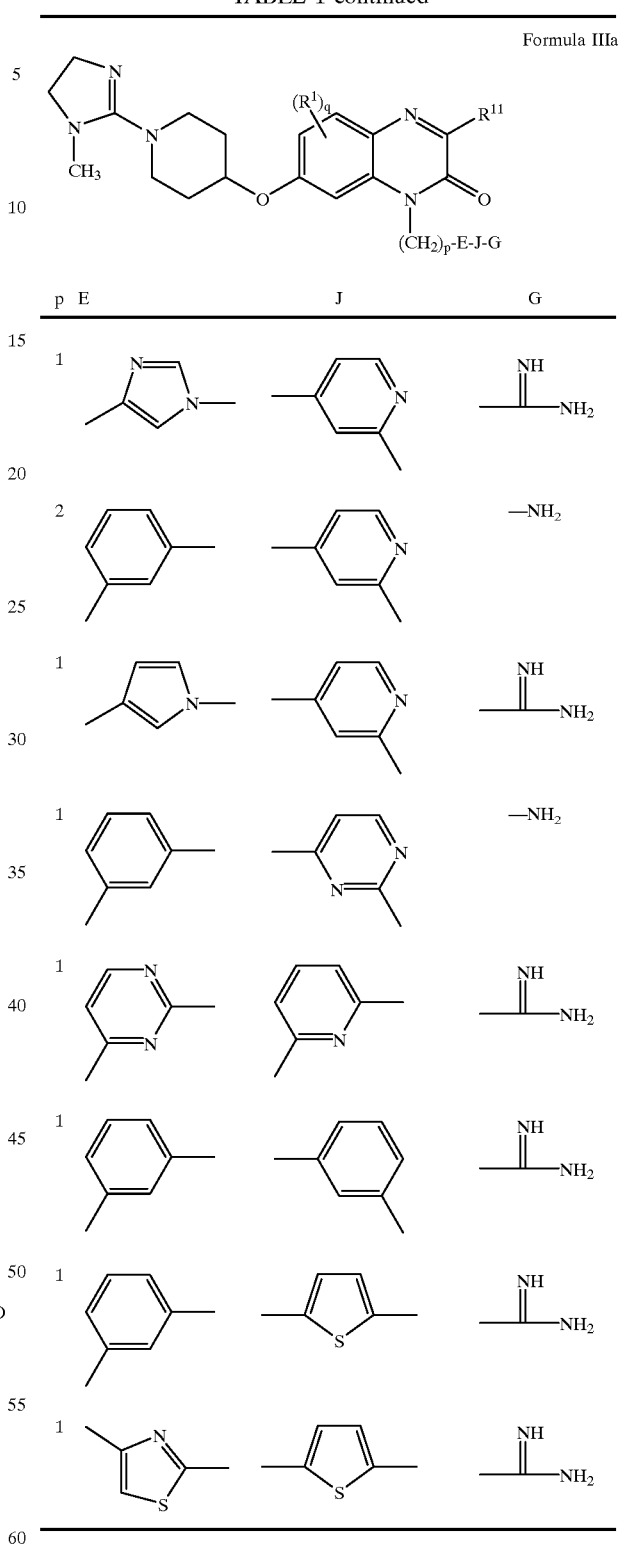

Also preferred compounds are compounds according to formula II wherein D is —O—, p and q are each an integer from 1 to 3, and E and J collectively form a substituted or unsubstituted biphenylene group. More preferred compounds having such an biphenylene group are compounds according to formula IV as set forth below:

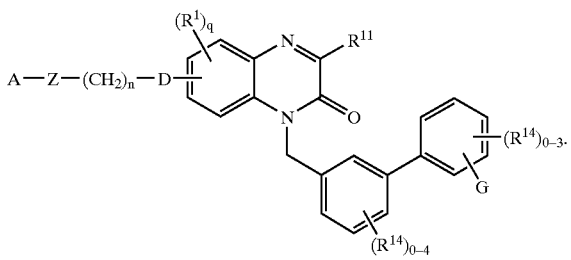

(IV)

In formula (IV), A, Z, n, D, $R^1$, q, $R^{11}$, G, and $R^{14}$ are each as defined for the compound of formula II as set forth above.

Particularly preferred compounds according to formula IV are compounds wherein each of the $R^1$, $R^8$, $R^{11}$ and $R^{14}$ groups is independently selected from the group consisting of hydrogen and $C_1$–$C_5$ alkyl, more preferably, hydrogen and $C_1$–$C_3$ alkyl, most preferably, hydrogen, methyl and ethyl.

Even more preferred compounds according to formula IVa as set forth in table 2 below, wherein each of the $R^1$, $R^8$, $R^{11}$ and $R^{14}$ groups are independently a member selected from the group consisting of hydrogen, methyl and ethyl and the remaining substituents are as set forth in Table 2, below.

TABLE 2

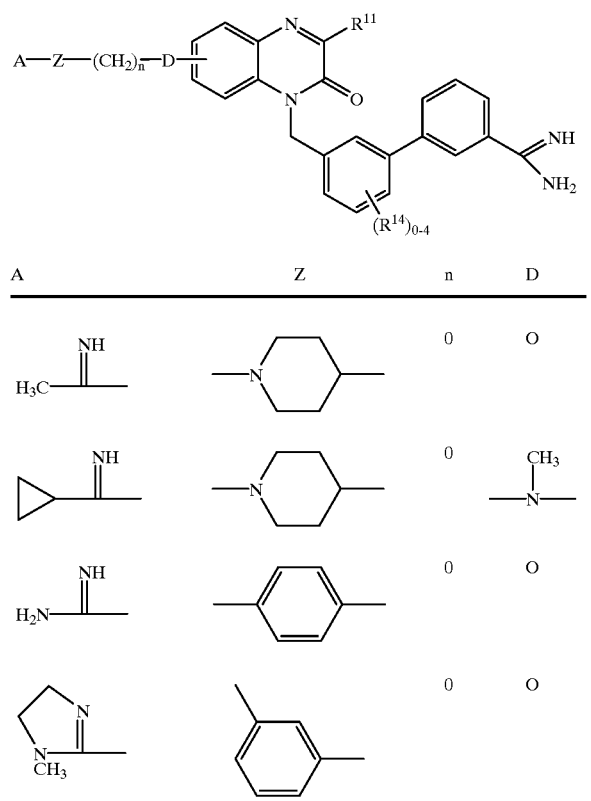

Also preferred compounds are compounds according to formula II where the bicyclic lactam ring structure is bound directly or indirectly (via linker group) to a saturated heterocyclic ring containing a nitrogen atom. Particularly preferred are compounds of formula II containing both a bicyclic lactam ring structure and a piperidine ring where D is —O—, p and q are each 1 to 3 and each of the remaining variables or substituents is defined as set forth in formula II as illustrated by formula V below:

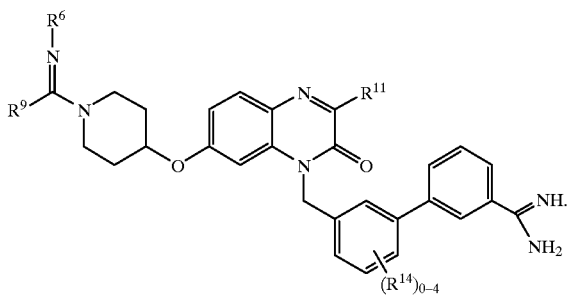

(V)

The invention also encompasses all pharmaceutically acceptable salts, hydrates, solvates, and prodrug derivatives of the compounds of the invention. In addition, the compounds of the invention can exist in various isomeric and tautomeric forms, and all such forms are meant to be included in the invention, along with pharmaceutically acceptable salts, hydrates, solvates and prodrug derivatives of such isomers and tautomers.

The compounds of the invention may be isolated as the free acid or base or converted to salts of various inorganic and organic acids and bases. Such salts are within the scope of the invention. Nontoxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

The invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of the invention which have groups cleavable under metabolic conditions. Prodrugs become the compounds of the invention which are pharmaceutically active in vivo, when they undergo solvolysis under physiological conditions or undergo enzymatic degradation. Prodrug compounds of the invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of the invention may be combined with other features herein taught to enhance bioavailability.

The compounds of the present invention may be use alone or in combination, or in combination with other therapeutic or diagnostic agents. In certain preferred embodiments, the compounds of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of the invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of the invention will typically utilize formulations in the form of solutions or suspensions. In the management of thrombotic disorders the compounds of the invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of the invention can be administered dosages that will provide optimal efficacy. The dose, i.e., the therapeutically effective amount, and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Preparation of Compounds

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

One exemplary synthesis scheme is outlined directly below, and the specific steps are described in the Examples. The reaction products are isolated and purified by conventional methods, typically by solvent extraction into a compatible solvent. The products may be further purified by column chromatography or other appropriate methods.

etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as

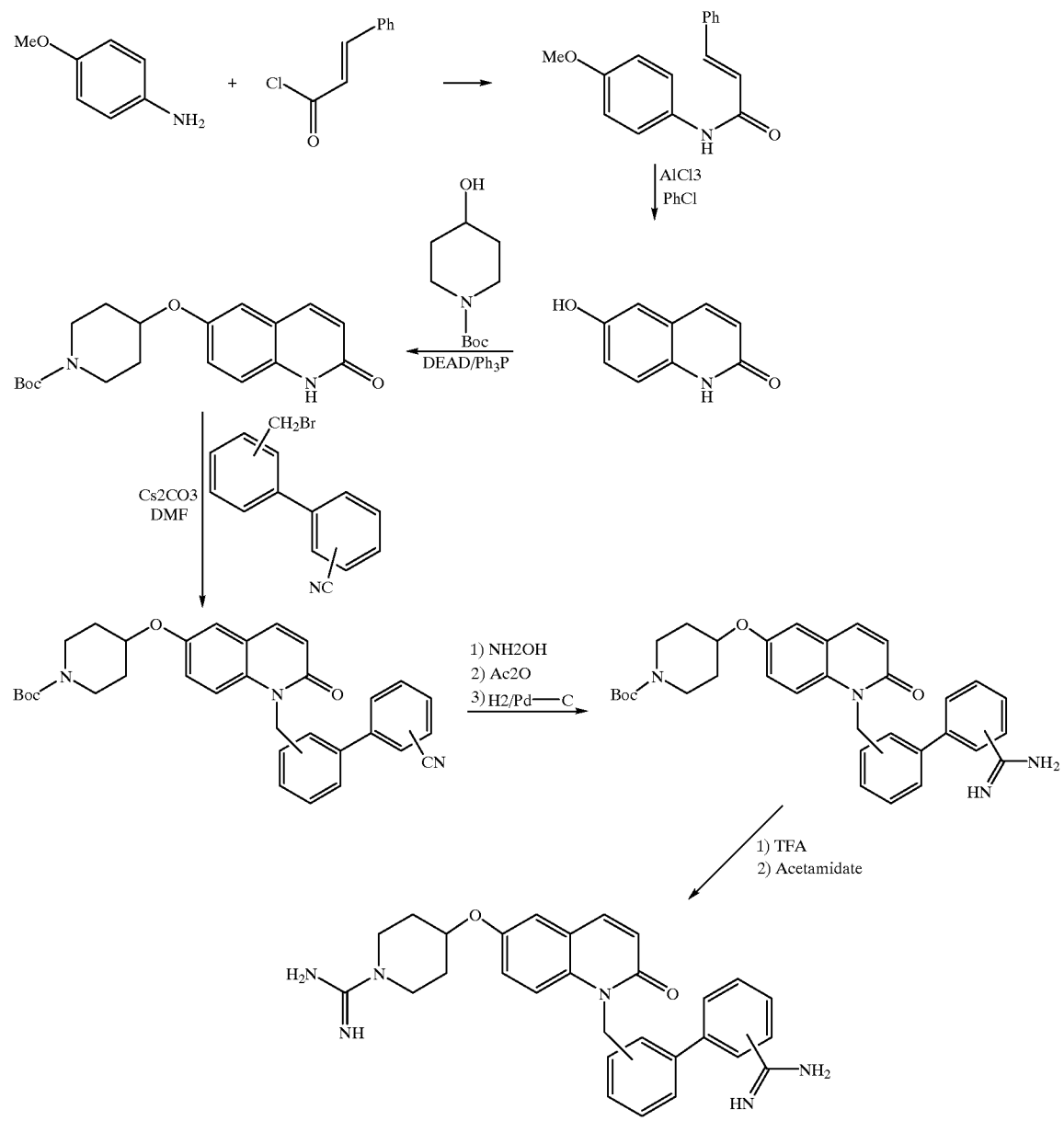

Composition or Formulations

Compositions or formulations of the compounds of the invention may be prepared for storage or administration by mixing a compound of the invention having a desired degree of purity with a pharmaceutically acceptable carrier or a physiologically acceptable carriers, excipients, stabilizers etc., polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN®, PLURONICS® or polyethyleneglycol.

Dosage formulations of the compounds of the invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of the invention typically will be about 3–11, more preferably about 5–9 and most preferably about 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of the invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of the invention may also be delivered by the use of antibodies, antibody fragments, growth factors, hormones, or other targeting moieties, to which the compound molecules are coupled. The compounds of the invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds and compositions/formulations of the invention can be administered orally or parenterally in an effective amount within the dosage range of about 0.001 to about 1000 mg/kg, preferably from about 0.01 mg/kg to about 100 mg/kg, most preferably, from about 0.10 to about 20 mg/kg. Advantageously, the compounds of the invention may be administered several times daily, and other dosage regimens may also be useful (e.g. single daily dose and/or continuous infusion).

Typically, about 0.5 to about 500 mg of a compound or mixture of compounds of the invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Applications

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of the invention are useful for the treatment or prophylaxis of those diseases which involve the production and/or action of factor Xa/prothrombinase complex. The compounds of this present invention, selected and used as disclosed herein, find utility as a diagnostic or therapeutic agent for preventing or treating a condition in a mammal characterized by undesired thrombosis or a disorder of coagulation. Disease states treatable or preventable by the administration of compounds of the invention include, without limitation, occlusive coronary thrombus formation resulting from either thrombolytic therapy or percutaneous transluminal coronary angioplasty, thrombus formation in the venous vasculature, disseminated intravascular coagulopathy, the treatment of reocclusion or restenosis of reperfused coronary arteries, thromboembolic complications of surgery and peripheral arterial occlusion, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

Accordingly, the invention provides a method for preventing or treating a condition in a mammal characterized by undesired thrombosis which administers to a mammal a therapeutically effective amount of a compound of the invention, as described herein. Conditions for prevention or treatment include, for example, (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multiorgan failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of the invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like. Thus, the compounds of the invention also find utility in a method for inhibiting the coagulation of biological samples by administration of a compound of the invention.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

Biological Activity Examples

Evaluation of the compounds of the invention is guided by in vitro protease activity assays (see below) and in vivo studies to evaluate antithrombotic efficacy, and effects on hemostasis and hematological parameters (see below).

The compounds of the present invention are dissolved in buffer to give solutions containing concentrations such that assay concentrations range from about 0 to about 100 $\mu$M. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving about 50% inhibition of the substrate turnover. The compounds of the present invention desirably have an $IC_{50}$ of less than about 500 nM in the factor Xa assay, preferably less than about 200 nM, and more preferred compounds have an $IC_{50}$ of about about 100 nM or less in the factor Xa assay. The compounds of the present invention desirably have an $IC_{50}$ of less than about 4.0 $\mu$M in the prothrombinase assay, preferably less than about 200 nM, and more preferred compounds have an $IC_{50}$ of about 10 nM or less in the prothrombinase assay. The compounds of the present invention desirably have an $IC_{50}$ of greater than about 1.0 $\mu$M in the thrombin assay, preferably greater than about 10.0 $\mu$M, and more preferred compounds have an $IC_{50}$ of greater than about 100.0 $\mu$M in the thrombin assay.

Amidolytic Assays for Determining Protease Inhibition Activity

The factor Xa and thrombin assays are performed at room temperature, in 0.02 M Tris·HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and are determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427–436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 $\mu$M) in 20 mM Tris·HCl buffer, pH 7.5, containing 0.15 M NaCl, 5 mM $CaCl_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex is used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithroimbotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in a Rabbit Venous Thrombosis Model

Administration of compounds in the rabbit venous thrombosis model demonstrates antithrombotic efficacy at the higher doses evaluated. There are no significant effects of the compounds on the aPTT and PT prolongation with the highest dose (100 μg/kg+2.57 μg/kg/min). Compounds have no significant effects on hematological parameters as compared to saline controls. All measurements are an average of all samples after steady state administration of vehicle or (D)-Arg-Gly-Arg-thiazole. Values are expressed as mean ±SD.

The following examples are non-limiting embodiments of the present invention, which were made utilizing a method as generally shown in reaction Scheme 1, above, or by a similar procedure.

EXAMPLES

Examples 1–19 are compounds according to the following formula:

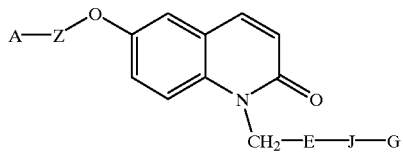

| Example | A-Z | E-J-G |
|---------|-----|-------|
| 1 | | |
| 2 | | |
| 3 | | |
| 4 | | |

-continued

| Example | A-Z | E-J-G |
|---------|-----|-------|
| 5 | 4-methylpiperidine | 3'-methyl-[1,1'-biphenyl]-3-carboxamidine |
| 6 | 4-methylpiperidine | 4'-methyl-[1,1'-biphenyl]-3-carboxamidine |
| 7 | 1-(1-iminoethyl)-4-methylpiperidine | 4'-methyl-[1,1'-biphenyl]-3-carboxamidine |
| 8 | 4-methylpiperidine | 1-(2'-methyl-[1,1'-biphenyl]-4-yl)ethanimine |
| 9 | 1-(1-iminoethyl)-4-methylpiperidine | 2'-methyl-[1,1'-biphenyl]-3-carboxamidine |
| 10 | 1-(1-iminoethyl)-4-methylpiperidine | 2'-methyl-[1,1'-biphenyl]-4-carboxamidine |
| 11 | 4-methylpiperidine | 2'-methyl-[1,1'-biphenyl]-3-carboxamidine |

-continued

| Example | A-Z | E-J-G |
|---------|-----|-------|
| 12 | 4-methylpiperidine (NH) | 4'-methyl-biphenyl-4-carboxamidine |
| 13 | 1-(ethanimidoyl)-4-methylpiperidine | 4'-methyl-biphenyl-4-carboxamidine |
| 14 | 1-(ethanimidoyl)-4-methylpiperidine | 1-ethyl-2-methyl-1H-indole-6-carboxamidine |
| 15 | 1-(ethanimidoyl)-4-methylpiperidine | 3'-methyl-biphenyl-4-carboxamidine |
| 16 | 1,4-dimethylpiperidine | 7-methyl-naphthalene-2-carboxamidine |
| 17 | 1-(ethanimidoyl)-4-methylpiperidine | 1-ethyl-2-methyl-1H-indole-6-carbohydrazonamide |
| 18 | 4-methyl-1-(pyrimidin-2-yl)piperidine | 7-methyl-naphthalene-2-carboxamidine |
| 19 | 1-(ethanimidoyl)-4-methylpiperidine | 3-propyl-benzamidine |

Below is biological data reported as IC$_{50}$ values, as described herein, for each of the compound Examples 1–19, shown above.

| Example | XA | IIA | IIASE | TRYPSIN | TPA | APC | PLASMIN | KALLIKREIN |
|---------|------|------|--------|---------|------|------|---------|------------|
| 1 | 0.151 | 122 | 9.11 | 0.0772 | 14.4 | 16.5 | 1.35 | 0.219 |
| 2 | 0.00562 | 50.2 | 0.0829 | 0.022 | 3.78 | 5.67 | 1.639 | 0.102 |

-continued

| Example | XA | IIA | IIASE | TRYPSIN | TPA | APC | PLASMIN | KALLIKREIN |
|---|---|---|---|---|---|---|---|---|
| 2 | 0.0115 | 28 | 0.179 | 0.00449 | 3.72 | 4.06 | 1.107 | 0.048 |
| 4 | 0.0118 | 4.56 | 0.157 | 0.0477 | 1.65 | 7.18 | 1.72 | 0.144 |
| 5 | 1.57 | 6.59 | 46.3 | 0.263 | | | | |
| 6 | 4.94 | 58.8 | 38.2 | 3.63 | | | | |
| 7 | 0.0823 | 45 | 0.362 | 4.29 | 69.7 | 56.9 | 10.1 | 1.95 |
| 8 | 500.99 | 1.7 | 1.92 | 56.6 | | | | |
| 9 | 2.55 | 0.885 | 0.697 | 0.847 | | | | |
| 10 | 137 | 0.995 | 1.2 | 52.5 | | | | |
| 11 | 41.9 | 2.48 | 2.18 | 0.289 | | | | |
| 12 | 70 | 9.13 | 15.5 | 4.41 | | | | |
| 13 | 50 | 3 | 8.63 | 1.91 | | | | |
| 14 | 0.00474 | 0.0693 | 0.0143 | 0.0104 | 0.34 | 0.13 | 0.316 | 0.064 |
| 15 | 18.8 | 30.4 | 33.5 | 3.37 | | | | |
| 16 | 0.209 | 399 | 2.58 | 0.315 | | | | |
| 17 | 0.514 | 11 | 1.21 | 0.832 | | | | |
| 18 | 0.58 | 75 | 3.25 | 0.656 | | | | |
| 19 | 0.015 | 68.9 | 2.3 | 0.582 | | | | |

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of formula III:

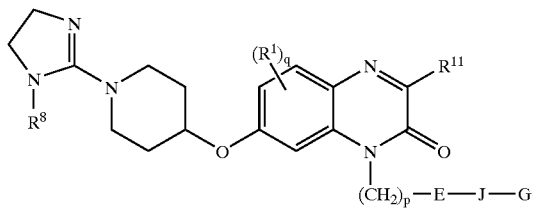

(III)

wherein:
$R^8$ is selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S;

$R^1$ is a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-C(=O)OH, $C_{1-8}$alkyl-OH, $C_{0-8}$alkyl-C(=O)O—$C_{1-8}$alkyl, —CN, —NO$_2$, $C_{0-8}$alkyl-SH, —C(=O) NR$^2$R$^3$—O—R$^2$ and O—C(=O)R$^2$, an unsubstituted amino group, a mono or disubstituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, —SO$_2$R$^2$, $C_{0-8}$alkyl-C(=O)OH and $C_{0-8}$alkyl-C(=O)O—$C_{1-8}$alkyl;

$R^2$ $R^3$ are independently selected from the group consisting o H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membereee heterocyclic ring system having 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S;

q is 0–3;

$R^{11}$ is a member selected from the group consisting of H, $C_{1-8}$alkyl, $C_{2-8}$alkenyl, $C_{2-8}$alkynyl, $C_{3-8}$cycloalkyl, $C_{6-12}$carbocyclic aryl, $C_{1-6}$alkylaryl, $C_{1-6}$alkyl-$C_{3-8}$ cycloalkyl, —O—R$^2$, —O—C(=O)R$^2$, —$C_{1-8}$alkyl-O—R$^{10}$, —$C_{1-8}$alkyl-O—C(=O)OR$^{10}$, —$C_{1-8}$alkyl-C(=O)OR$^{10}$, —$C_{1-8}$alkyl-O—C(=O)OR$^{10}$, $C_{1-8}$alkyl-C(=O) NR$^{10}$R$^{10}$, —OR$^{10}$, —$C_{1-8}$alkyl-NR$^{10}$R$^{10}$, —$C_{1-8}$alkyl-NR$^{10}$C(=) OR$^{10}$, —SR$^{10}$, where R$^2$ is as described and R$^{10}$ is a member selected from the group consisting of H, $C_{1-8}$alkyl, $C_{2-8}$alkenyl, $C_{2-8}$alkynyl, and wherein when two R$^{10}$ groups are present they may be taken together to form a saturated or unsaturated ring with the atom to which they are both attached;

p is an integer from 0–2;

E is a member selected from the group consisting of a direct link, —O—, —N(R$^{11}$)—, where R$^{11}$ is as set forth above, phenylene, a bivalent 5 to 12 member heteroaryl group containing 1 to 4 heteroatoms selected from the group consisting of N, O and S, and a five to ten membered non-aromatic bivalent heterocyclic ring system having 1–4 heteroatoms selected from the group consisting of N, O and S, wherein said heteroaryl and said non-aromatic heterocyclic ring structure may be independently substituted by from 0 to 5 R$^{14}$ groups;

J is a member selected from the group consisting of a direct link, a bivalent $C_{3-8}$cycloalkyl group, phenylene, a 5 to 12 member bivalent heteroaryl group having 1 to 4 heteroatoms selected from the group consisting of N, O and S, and a five to ten membered non-aromatic bivalent heterocyclic ring system containing 1–4 heteroatoms selected from the group consisting of N, O and S wherein said heteroaryl and said non-aromatic heterocyclic ring structure may be independently substituted by from 0 to 5 R$^{14}$ groups;

each R$^{14}$ group is a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-C (=O)OH, $C_{0-8}$alkyl-C(=O)O—$C_{1-8}$alkyl, —CN, —NO$_2$, $C_{0-8}$alkyl-OH, $C_{1-8}$alkyl-SH, —O—R$^2$ and —O—C(=O)R$^2$, an unsubstituted amino group, a mono or disubstituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, $C_{0-8}$alkyl-C(=O)OH and $C_{0-8}$alkyl-C(=O)O—$C_{1-8}$alkyl;

G is a member selected from the group consisting of: H; —CN; —OR$^{17}$;

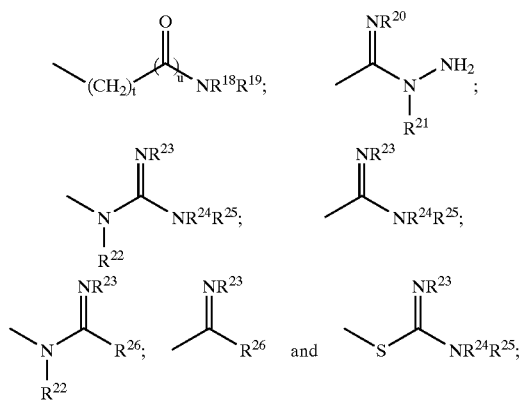

wherein t is an integer from 0 to 6, u is the integer 0 or 1, and R$^{17}$, R$^{18}$, R$^{19}$, R$^{20}$, R$^{21}$, R$^{22}$, R$^{23}$, R$^{24}$, R$^{25}$ and R$^{26}$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where R$^{18}$ taken with R$^{19}$, R$^{22}$ taken with either of R$^{24}$ and R$^{25}$, and R$^{24}$ taken with R$^{25}$, can each independently form a 5 to 6 membered heterocyclic ring containing from 1 to 4 atoms selected from the group consisting of N, O and S;

with the proviso that when G is H, —CN, —OR$^{17}$, either E or J must contain at least one N atom;

and all pharmaceutically acceptable isomers, salts, hydrates, solvates and prodrug derivatives thereof.

2. A compound of claim 1, wherein R$^1$ and R$^8$ are independently a lower alkyl group and R$^{11}$ is hydrogen or is a $C_1$ to $C_8$ alkyl group.

3. A compound of claim 1, wherein q is zero and R$^8$ is lower alkyl group.

4. A compound of claim 1, wherein:

R$^8$ is a methyl group;

p is an integer from 1–2;

E is selected from the group consisting of: a direct link,

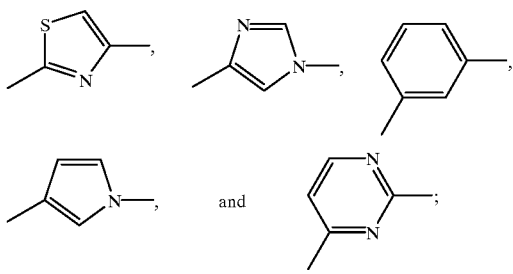

J is selected from the group consisting of:

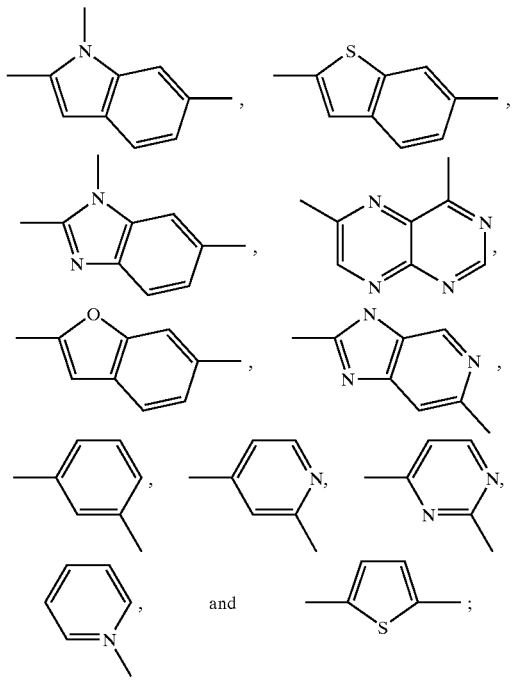

and G is selected from the group consisting of:

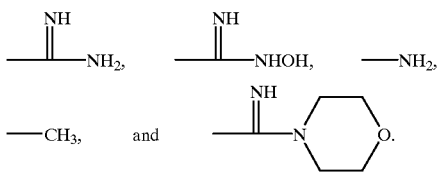

5. A compound of formula IV:

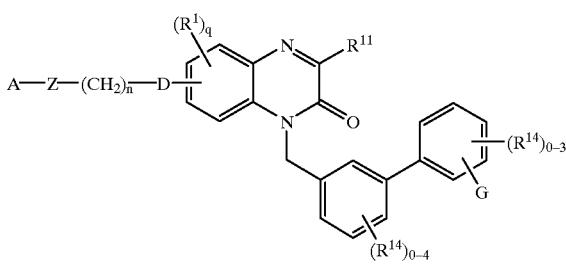

wherein:

A is a member selected from the group consisting of: $R^2$, $-NR^3R^4$, $-C(=O)NR^3R^4$,

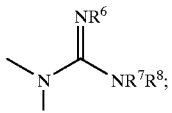 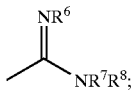

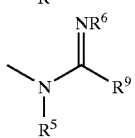 and 

where $R^2$, $R^3$, $R^4$, $R^5$, $R^6$, $R^7$, $R^8$, and $R^9$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system containing 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $R^6$ taken with either of $R^7$ and $R^8$, and/or $R^7$ taken with $R^8$, can each form a 5 to 6 membered heterocyclic ring containing from 1 to 4 atoms selected from the group consisting of N, O and S;

Z is a member selected from the group consisting of a direct link, $C_{1-8}$alkyl, $C_{3-8}$cycloalkyl, $C_{2-8}$alkenyl, $C_{2-8}$alkynyl, $C_{1-8}$carbocyclic aryl, or a five to ten membered heterocyclic ring system containing 1–4 heteroatoms selected from the group consisting of N, O and S;

n is 0–3;

D is a member selected from the group consisting of: $-CH_2-$, $-O-$, $-NR^2$, $C(=O)-$, $-S-$, $-SO_2-$, $-SO_2-NR^2$, $-NR^2-SO_2$, $-OC(=O)-$, $-C(=O)NR^2$, and $-NR^2-C(=O)-$;

$R^1$ and $R^{14}$ are independently a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-C(=O)OH, $C_{0-8}$alkyl-C(=O)O—$C_{1-8}$alkyl, —CN, —NO$_2$, $C_{1-8}$alkyl-OH, $C_{0-8}$alkyl-SH, —O—$R^2$ and —O—C(=O)$R^2$, an unsubstituted amino group, a mono- or di-substituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, $C_{0-8}$alkyl-C(=O)OH and $C_{0-8}$alkyl-C(=O)O—$C_{1-8}$alkyl;

q is 0–3;

$R^{11}$ is a member selected from the group consisting of H, $C_{1-8}$alkyl, $C_{2-8}$alkenyl, $C_{2-8}$alkynyl, $C_{3-8}$cycloalkyl, $C_{6-12}$carbocyclic aryl, $C_{1-6}$alkylaryl, $C_{1-6}$alkyl-$C_{3-8}$cycloalkyl, —O—$R^2$, —O—C(=O)$R^2$, $C_{1-8}$alkyl-O—$R^{10}$, —$C_{1-8}$alkyl- O—(=O)$R^{10}$, —$C_{1-8}$alkyl-C(=O) O$R^{10}$, —$C_{1-8}$alkyl-O—C(=O)O$R^{10}$, $C_{1-8}$alkyl-C(=O)N$R^{10}R^{10}$, —$C_{1-8}$alkyl-N$R^{10}R^{10}$, —$C_{1-8}$alkyl-N$R^{10}$C(=O)$R^{10}$, —S$R^{10}$, where $R^2$ is as describe and $R^{10}$ is a member selected from the group consisting of H, $C_{1-8}$alkyl, $C_{2-8}$alkenyl, $C_{2-8}$alkynyl, and wherein when form a saturated or unsaturated ring with the atom to which they are both attached;

G is a member selected from the group consisting of:

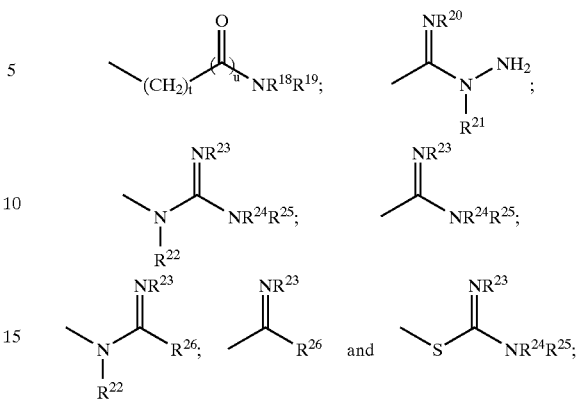

wherein t is an integer from 0 to 6, u is the integer 0 or 1, and $R^{17}$, $R^{18}$, $R^{19}$, $R^{20}$, $R^{21}$, $R^{22}$, $R^{23}$, $R^{24}$, $R^{25}$ and $R^{26}$ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system having 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S; where $R^{18}$ taken with $R^{19}$, $R^{22}$ taken with either of $R^{24}$ and $R^{25}$, and $R^{24}$ taken with $R^{25}$, can each independently form a 5 to 6 membered heterocyclic ring having from 1 to 4 atoms selected from the group consisting of N, O and S;

or a pharmaceutically acceptable diastereomer, salt, hydrate, and solvate thereof.

6. A compound of claim 5, wherein $R^1$, $R^8$, $R^{11}$ and $R^{14}$ are independently selected from the group consisting of hydrogen, methyl and ethyl;

A is selected from the group consisting of: —H, —CH$_3$, —NH$_2$, —C(O)N(CH$_3$)$_2$,

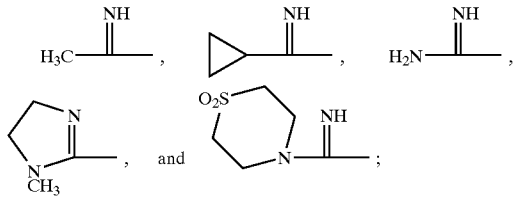

Z is selected from the group consisting of:

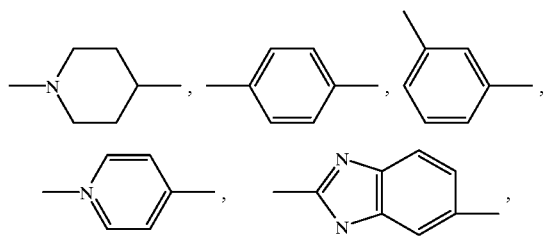

-continued

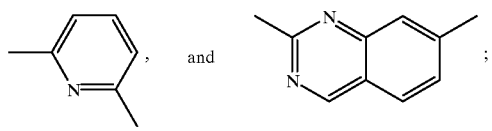

n is an integer from 0–2; and
D is selected from the group consisting of: —O—, —N(CH₃)—, and —CH₂—.

7. A compound of formula V:

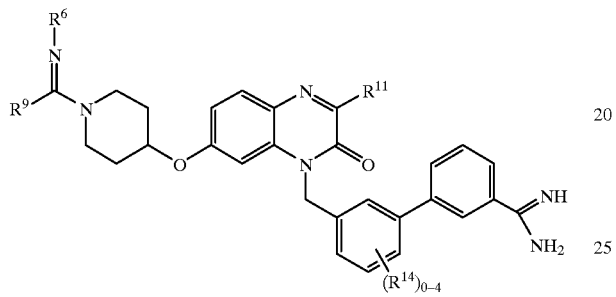

(V)

wherein:

R², R⁶, and R⁹ are independently selected from the group consisting of H, —OH, $C_{1-8}$alkyl, $C_{2-8}$alkenyl, $C_{2-8}$alkynyl, $C_{3-8}$cycloalkyl, $C_{6-12}$carbocyclic aryl, a five to ten membered heterocyclic ring system having 1–4 heteroatoms selected from the group consisting of N, O and S; and $C_{1-6}$alkylheterocyclic ring system having in the ring system 5 to 10 atoms with 1 to 4 of such atoms being selected from the group consisting of N, O and S;

R¹¹ is independently a member selected from the group consisting of H, $C_{1-8}$alkyl, $C_{2-8}$alkenyl, $C_{2-8}$alkynyl, $C_{3-8}$cycloalkyl, $C_{6-12}$carbocyclic aryl, $C_{1-6}$alkylaryl, $C_{1-6}$alkyl-$C_{3-8}$cycloalkyl, —O—R², —O—C(=O)R², —$C_{1-8}$alkyl-O—R¹⁰, —$C_{1-8}$alkyl-O—C(=O)R¹⁰, —$C_{1-8}$alkyl-C(=O)OR¹⁰, $C_{1-8}$alkyl-O—C(=O)OR¹⁰, —$C_{1-8}$alkyl-C(=O)NR¹⁰R¹⁰, —$C_{1-8}$alkyl-NR¹⁰R¹⁰, —$C_{1-8}$alkyl-NR¹⁰C(=O)R¹⁰, —SR¹⁰, where R² is as described above and R¹⁰ is a member selected from the group consisting of H, $C_{1-8}$alkyl, $C_{2-8}$alkenyl, $C_{2-8}$alkynyl, and wherein when two R¹⁰ groups are present they may be taken together to form a saturated or unsaturated ring with the atom to which they are both attached;

each R¹⁴ group is a member selected from the group consisting of H, $C_{1-8}$alkyl, $C_{2-8}$alkenyl, $C_{2-8}$alkynyl, $C_{3-8}$cycloalkyl, halogen, polyhaloalkyl, $C_{0-8}$alkyl-C(=O)OH, $C_{0-8}$alkyl-C(=O)O—$C_{1-8}$alkyl, —CN, —NO₂, $C_{0-8}$alkyl-OH, $C_{0-8}$alkyl-SH, —O—R² and —O—C(=O)R², an unsubstituted amino group, a mono or di-substituted amino group, wherein the substituted amino groups are independently substituted by at least one member selected from the group consisting of H, $C_{1-8}$alkyl, $C_{2-8}$alkenyl, $C_{2-8}$alkynyl, $C_{3-8}$cycloalkyl, polyhaloalkyl, $C_{0-8}$alkyl-C(=O)OH and $C_{0-8}$alkyl-C(=O)O—$C_{1-8}$alkyl;

or a pharmaceutically acceptable diastereomer, salt, hydrate, and solvate thereof.

8. A compound having the following structure:

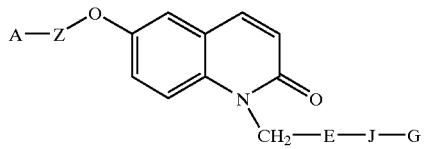

wherein:

A—Z is a member selected from the group consisting of:

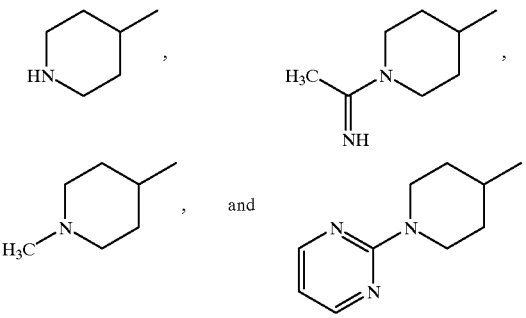

E—J—G is a member selected from the group consisting of:

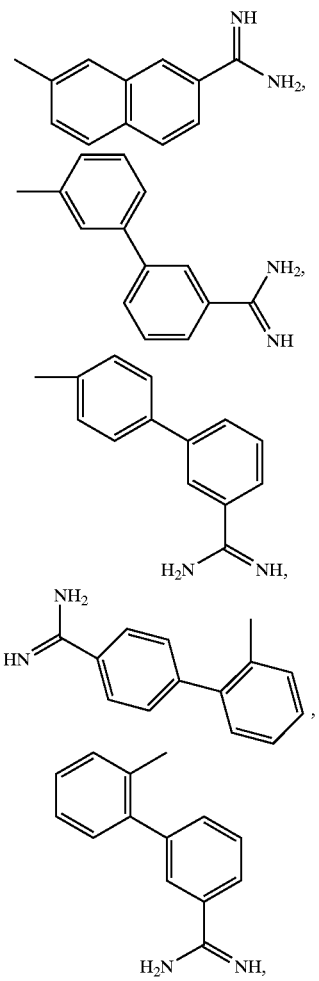

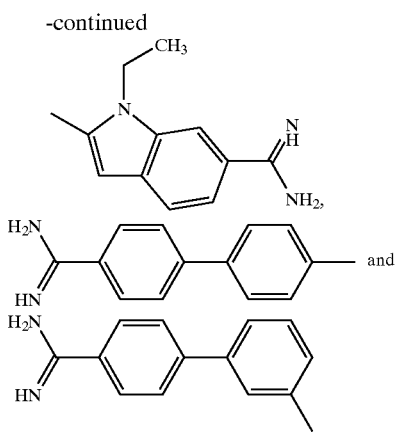

and all pharmaceutically acceptable isomers, salts, hydrates, solvates and prodrug derivatives thereof.

9. A pharmaceutical composition for treating a condition in a mammal characterized by undesired thrombosis comprising a pharmaceutically acceptable carrier and a therapeutically effective amount of a compound as in one of claims 1–8.

10. A method for treating a condition in a mammal characterized by undesired thrombosis comprising administering to said mammal a therapeutically effective amount of a compound as in one of claims 1–8.

11. The method of claim 10, wherein the condition is selected from the group consisting of:

acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with an intra-aortic balloon pump, a coronary stent, cardiac valve, or prosthetic devices.

12. A method for inhibiting the coagulation of biological samples comprising the administration of a compound as in one of claims 1–8.

* * * * *